(12) United States Patent
Merante

(10) Patent No.: US 10,392,654 B2
(45) Date of Patent: Aug. 27, 2019

(54) SITE-SPECIFIC ENDONUCLEASE GUIDED ROLLING CIRCLE AMPLIFICATION

(71) Applicant: Simply Diagnostics Inc., Richmond Hill (CA)

(72) Inventor: Francesco Merante, Etobicoke (CA)

(73) Assignee: Simply Diagnostics Inc., Richmond Hill, Ontario (CA)

( * ) Notice: Subject to any disclaimer, the term of this patent is extended or adjusted under 35 U.S.C. 154(b) by 0 days.

(21) Appl. No.: 15/500,279

(22) PCT Filed: Jul. 28, 2015

(86) PCT No.: PCT/CA2015/050714
§ 371 (c)(1),
(2) Date: Jan. 30, 2017

(87) PCT Pub. No.: WO2016/019455
PCT Pub. Date: Feb. 11, 2016

(65) Prior Publication Data
US 2017/0211137 A1 Jul. 27, 2017

Related U.S. Application Data

(60) Provisional application No. 62/029,923, filed on Jul. 28, 2014.

(51) Int. Cl.
*C12Q 1/68* (2018.01)
*C12P 19/34* (2006.01)
(Continued)

(52) U.S. Cl.
CPC ......... *C12Q 1/6844* (2013.01); *C12Q 1/6853* (2013.01)

(58) Field of Classification Search
None
See application file for complete search history.

(56) References Cited

FOREIGN PATENT DOCUMENTS

WO WO2006/074162 A2 7/2006

OTHER PUBLICATIONS

Dominguez et al., "Wild-type blocking polymerase chain reaction for detection of single nucleotide minority mutations from clinical specimens", Oncogene, vol. 24, pp. 6830-6834 (Year: 2005).*

(Continued)

*Primary Examiner* — Young J Kim
(74) *Attorney, Agent, or Firm* — Bereskin & Parr LLP/S.E.N.C.R.L., s.r.l.; I Laurence MacPhie

(57) ABSTRACT

The disclosure provides methods and kits involving site-specific endonuclease guided rolling circle amplification (RCA). Nucleic acid substrates, optionally generated by hybridizing a guidance primer to a single stranded nucleic acid, are cleaved with a site-specific endonuclease. In the presence of the target site, endonuclease cleavage of the substrate generates a nucleic acid having a free 3'-hydroxyl end, which is allowed to hybridize to covalently closed circular DNA probe ("take-off probe"), and initiate a rolling circle amplification (RCA) reaction. The methods and kits may be used to detect the presence of a target nucleic acid sequence, including detection of single nucleotide polymorphisms, and may be used to assess methylation status of a desired sequence, assess zygosity and/or ploidy status. The methods and kits may also be used to detect nucleic acids associated or indicative of medical conditions or pathogenic organisms.

17 Claims, 6 Drawing Sheets
Specification includes a Sequence Listing.

(51) Int. Cl.
   *C12Q 1/6844*   (2018.01)
   *C12Q 1/6853*   (2018.01)

(56) References Cited

OTHER PUBLICATIONS

Sood et al., "Terminal Phosphate-Labeled Nucleotides with Improved Substrate Properties for Homogeneous Nucleic Acid Assay," JACS, vol. 127, pp. 2394-2395. (Year: 2005).*
Ayers et al., "A single tube RT-PCR assay for the detection of mosquito-borne flaviviruses," Journal of Virological Methods, vol. 135, pp. 235-239. (Year: 2006).*
Ausubel, F.M. et al., "Current Protocols in Molecular Biology", John Wiley & Sons, N.Y., 1989, 6.3.1-6.3.6.
Dean, F.B., et al., "Rapid Amplification of Plasmid and Phage DNA Using Phi29 DNA Polymerase and Multiply-Primed Rolling Circle Amplification", Genome Res., 2001, 11, pp. 1095-1099.
Donis-Keller, H., "Site specific enzymatic cleavage of RNA", Nucleic Acids Res., Sep. 11, 1979, vol. 7, No. 1, pp. 179-192.
Gill, P., and Ghaemi, A., "Nucleic acid isothermal amplification technologies—a review." Nucleosides, Nucleotides and Nucleic Acids, 2008, vol. 27, pp. 224-243.
Kuhn, H., et al., "Artificial Site-Specific DNA-Nicking System Based on Common Restriction Enzymes Assisted by PNA Openers." Biochemistry, Apr. 10, 2003, vol. 42(17), pp. 4985-4992.
Larsson, C., et al., "In situ genotyping individual DNA molecules by target-primed rolling-circle amplification of padlock probes", Nature Methods, Nov. 18, 2004, vol. 1, No. 3, pp. 227-232.
Murakami, T., et al., "Sensitive isothermal detection of nucleic-acid sequence by primer generation-rolling circle amplification." Nucleic Acids Research, 2009, vol. 37, No. 3, e19. (A).
Murakami, T., et al., "Sensitive Nucleic Acid Detection by Primer Generation-Rolling Circle Amplification", EpiBio.com., CircLigase™ ssDNA Ligase, Jun. 2009, vol. 16-2. (B).
Murakami,T. et al., "Sensitive RNA detection by combining three-way junction formation and primer generation-rolling circle amplification." Nucleic Acids Research, 2012, vol. 40, No. 3, e22.
Zamore, P.D., et al., "RNAi: Double-Stranded RNA Directs the ATP-Dependent Cleavage of mRNA at 21 to 23 Nucleotide Intervals", Cell, Mar. 31, 2000, vol. 101, pp. 25-33.
International Search Report and Written Opinion for corresponding PCT Application No. PCT/CA2015/050714 dated Oct. 8, 2015.
Kobori, T., and Takahashi, H., "Expanding Possibilities of Rolling Circle Amplification as a Biosensing Platform." Analytical Sciences, Reviews, Jan. 2014, vol. 30, pp. 59-64.
Christian, A., et al., "Detection of DNA point mutations and mRNA expression levels by rolling circle amplification in individual cells." PNAS, Dec. 4, 2001, vol. 98, No. 25, pp. 14238-14243.
Zhong, X., et al. "Visualization of oligonucleotide probes and point mutations in interphase nuclei and DNA fibers using rolling circle DNA amplification." PNAS, Mar. 27, 2001, vol. 98, No. 7, pp. 3940-3945.
Lindstrom, U.M., et al., "Artificial human telomeres from DNA nanocircle templates." PNAS, Dec. 10, 2002, vol. 99, No. 25, pp. 15953-15958.

* cited by examiner

Recognition and Cleavage

Take-off primer binding

Isothermal amplification

DNA Polymerase + dNTPs

Lane 1: uncut M13 (+) DNA
Lane 2: M13 (+) DNA cut with Alu I
Lane 3: M13 (+) DNA cut with Alu I (1/5 dilution)
Lane 4: M13 (+) DNA cut with Alu I (1/10 dilution)
Lane 5: M13 (+) DNA cut with Alu I (1/20 dilution)
Lane 6: M13 (+) DNA cut with Alu I (1/40 dilution)
Lane 7: M13 (+) DNA cut with Alu I (1/80 dilution)
Lane 8: M13 (+) DNA cut with Alu I (1/100 dilution)
Lane 9: Negative control (water + MM)

SITE-SPECIFIC ENDONUCLEASE GUIDED ROLLING CIRCLE AMPLIFICATION

CROSS REFERENCE TO RELATED APPLICATIONS

This Application is a national phase entry of PCT/CA2015/050714 filed Jul. 28, 2015 (which designates the U.S.) which claims priority to U.S. Provisional Patent Application No. 62/029,923 filed Jul. 28, 2014, the contents of which are incorporated by reference herein in their entirety.

INCORPORATION OF SEQUENCE LISTING

A computer readable form of the Sequence Listing "23957-P46003US01_SequenceListing.txt" (4,096 bytes), submitted via EFS-WEB and created on Jan. 30, 2017, is herein incorporated by reference.

FIELD

The disclosure relates to methods and kits involving site-specific endonuclease guided rolling circle amplification.

INTRODUCTION

Numerous methods of nucleic acid amplification are known in the art. Typical methods require temperature cycling to denature a desired template, permitting primer binding and subsequent DNA synthesis by a DNA polymerase mediated extension reaction. These methods are exemplified by the polymerase chain reaction (PCR) in which nucleic acid extension occurs through a thermostable DNA polymerase. The product of this amplification reaction is generally a well-defined double stranded segment of amplified DNA.

Amplification methods that do not require temperature cycling utilize a single set temperature, termed isothermal amplification. The isothermal methodologies are effectively embodied by strand displacement type reactions such as the loop-mediated isothermal amplification procedure (LAMP), or helicase dependent amplification, to allow a suitable primer or sets of primers to hybridize to their target sequences and enable a DNA polymerase to initiate an extension reaction. Repeated rounds of strand displacement, annealing and extension effectively amplify a target sequence yielding double stranded, concatenated amplification products.

A second category of isothermal amplification occurs via a rolling circle type reaction in which a covalently closed circular probe, generated in a previous step or added as part of the reaction, hybridizes to a target sequence and commences extension around the circle to produce a string of repeating, concatenated-single-stranded sequences often hundreds to tens-of-thousands of bases long.

Isothermal rolling circle methods of target DNA amplification typically involve use of multiple primers, involving complicated primer design, to achieve targeted amplification. In many situations, access to specialized and costly instrumentation and/or DNA synthesis facilities may be lacking or prohibitively expensive.

Accordingly, there is a need for simplified methods for specific, targeted, and sensitive amplification that can be widely used, particularly in situ and at ambient temperatures, without requiring complicated primer design, with wide target specificity and which can be used with inexpensive and readily available reagents and minimal instrumentation.

SUMMARY

The present disclosure is directed to methods and kits involving the use of site-specific endonuclease guided rolling circle amplification. As described herein, a high degree of target specificity may be conferred by the combined requirement for endonuclease site-specific cleavage and sequence complementary between a free 3' end generated upon endonuclease cleavage and the circular DNA probe used as a template for rolling circle amplification. The methods described may simplify the number and complexity of primers or probes required for amplification, over conventional methods such as LAMP which require minimally four primers to perform the isothermal amplification. The methods described may also be readily adapted for isothermal amplification, for example, at uniform temperatures.

An aspect of the disclosure provides a method of nucleic acid amplification, comprising:
 a) providing a sample comprising a nucleic acid substrate, wherein the substrate comprises a recognition site recognized by a site-specific endonuclease;
 b) cleaving the substrate with the endonuclease;
 c) contacting the cleaved substrate with a circular DNA probe under conditions that allow for hybridization between complementary sequences of the cleaved substrate and the circular DNA probe; and
 d) generating an amplified nucleic acid product by rolling circle amplification (RCA).

In an embodiment, the RCA is primed by hybridization of a 3' region of the cleaved nucleic acid substrate to the circular DNA probe, wherein the 3' region comprises a free 3'-hydroxyl end generated upon cleavage of the substrate by the endonuclease. In one embodiment, generating an amplified nucleic acid product by RCA comprises contacting the cleaved substrate and circular DNA probe with deoxynucleotide-triphosphates (dNTPs) and a polymerase enzyme.

In one embodiment, the recognition site is a single stranded nucleic acid sequence. In another embodiment, the recognition site is a double stranded nucleic acid sequence. In yet another embodiment, the double stranded recognition site of the substrate comprises double stranded DNA, double stranded RNA, or DNA:RNA hybrid duplex.

In one embodiment, the nucleic acid substrate is a single stranded nucleic acid molecule. In another embodiment, the nucleic acid substrate is a double stranded nucleic acid molecule. In an embodiment, step a) comprises generating the nucleic acid substrate from a single stranded nucleic acid initiation strand. In yet another embodiment, the initiation strand is single stranded RNA, single stranded DNA, or a combination thereof.

In an embodiment, the initiation strand is a naturally occurring nucleic acid molecule or fragment thereof, or is an amplification product of a naturally occurring nucleic acid molecule or fragment thereof.

In another embodiment, a double stranded recognition sequence is generated by hybridizing a guidance primer to the initiation strand, wherein the guidance primer is a single stranded nucleic acid molecule comprising a sequence complementary to at least a portion of the initiation strand. In a preferred embodiment, the guidance primer does not bind to the circular DNA probe or serve as a primer for rolling circle amplification. In one embodiment, the target nucleic acid substrate is cleaved at a recognition site and a portion of the target nucleic acid substrate upstream of the recognition site with a free 3' hydroxyl end hybridizes to the circular DNA probe and serves as a primer for rolling circle amplification.

In one embodiment, the guidance primer is a non-naturally occurring synthetic nucleic acid molecule.

In another embodiment, the guidance primer is from 8 to 60 nucleotides in length, optionally from 12 to 20 nucleotides.

In an embodiment, generating the double stranded recognition site of the substrate from the initiation strand comprises synthesizing a complementary strand using the initiation strand as template.

In another embodiment, the complementary strand is synthesized using a DNA polymerase, DNA-dependent RNA polymerase, RNA-dependent RNA polymerase, or a reverse transcriptase.

In an embodiment, the RCA is primed by hybridization of a 3' region of the substrate, wherein the 3' region of the cleaved substrate is derived from the initiation strand.

In another embodiment, more than one RCA is primed by hybridization of more than one 3' region of the cleaved substrate to the circular DNA probe.

In yet another embodiment, the recognition site is a double stranded nucleic acid sequence, and wherein at least two of the 3' regions of the cleaved substrate are derived from different strands of the substrate. In one embodiment, two different cleavage products of the initiation strand hybridize to two different complementary regions on one or more circular DNA probes.

In one embodiment, the method comprises contacting the cleaved nucleic acid substrate with a circular DNA probe comprising a single sequence that is complementary to the 3' end of the nucleic acid substrate cleaved by the site specific endonuclease. In one embodiment, the method comprises contacting the cleaved nucleic acid with a circular DNA probe comprising a two or more sequences that are each complementary to the 3'end of the cleaved nucleic acid substrate. In one embodiment, the method comprises contacting the cleaved nucleic acid substrate with a circular DNA probe comprising two or more regions that are complementary to the 3' end of two or more initiation strands, optionally regions that are complementary to the 3' end of two or more different initiation strands. For example, in one embodiment, cleaving the nucleic acid substrate with the site specific endonuclease produces a cleavage product with a free 3' hydroxyl end that can hybridize to a complementary region on a circular DNA probe. In one embodiment cleaving the nucleic acid substrate with the site specific endonuclease produces two or more cleavage products with free 3' hydroxyl end that can hybridize to complementary regions on a circular DNA probe.

In one embodiment, the circular DNA probe comprises two or more sequences complementary to the same 3' sequence upstream of the recognition site. In one embodiment, the circular DNA probe comprises two or more regions complementary to different 3' sequences produced by cleavage of the nucleic acid substrate by the site specific endonuclease.

In an embodiment, the cleaved substrate is denatured prior to, or during, contacting with the circular DNA probe, optionally chemically and/or thermally denatured.

In one embodiment, one or more of steps a) to d) of the described methods occur at the same temperature or at different temperatures.

In another embodiment, one or more of steps a) to d) of the described methods occur at a substantially constant temperature.

In yet another embodiment, one or more of steps a) to d) of the described methods occur at the same substantially constant temperature.

In an embodiment, the substantially constant temperature is a temperature of from about 15° C. to about 85° C., from about 20° C. to about 72° C., less than about 70° C., less than about 65° C., less than about 40° C. and/or an ambient temperature.

In another embodiment, the RCA is linear RCA.

In yet another embodiment, the RCA occurs in the presence of an amplification primer, wherein the amplification primer is a nucleic acid molecule capable of hybridizing to the amplified nucleic acid product and initiating DNA synthesis using the amplified nucleic acid product as template.

In an embodiment, the amplification primer comprises a sequence at the 3' end of the amplification primer which is capable of hybridizing to a sequence complementary to the sequence of the circular DNA probe or a portion thereof.

In another embodiment, the methods described further comprise the step of detecting the amplified nucleic acid product, or nucleic acids amplified therefrom.

In an embodiment, the amplified nucleic acid product is detected in situ, in gel via electrophoresis, in a lateral flow, in microarray, and/or on a bead surface. In another embodiment, the detection involves labeling of the nucleic acids with a detectable label.

In yet another embodiment, the labeling involves use of fluorescent labeled nucleotides, hapten labeled nucleotides, fluorescent labeled probes, molecular beacons, fluorescent barcodes and/or fluorescent DNA binding dyes.

In one embodiment, the fluorescent DNA binding dye is a single strand specific fluorescent DNA binding dye or a double strand specific fluorescent DNA binding dye.

In another embodiment, the amplified product is detected in situ in real time.

In yet another embodiment, the site-specific endonuclease is a restriction endonuclease or a riboendonuclease.

In an embodiment, the endonuclease is a restriction endonuclease, and wherein the recognition site recognized by the restriction endonuclease is a nucleotide sequence in single-stranded DNA and wherein the restriction endonuclease cleaves single stranded DNA.

In another embodiment the endonuclease is a restriction endonuclease, and wherein the recognition site recognized by the restriction endonuclease is a double stranded nucleotide sequence, or a double-stranded DNA:RNA hybrid, and wherein the restriction endonuclease cleaves both strands of double stranded DNA, or both strands of a DNA:RNA hybrid.

In an embodiment, the riboendonuclease is RNase H.

Another aspect provides a method of detecting the presence of a target nucleic acid sequence in a test sample, wherein the target nucleic acid sequence comprises a recognition site recognized by a site-specific endonuclease. In one embodiment, the method comprises:

performing nucleic acid amplification according to the methods described herein, wherein the sample in step a) is a test sample, and wherein detection of an amplified nucleic acid product indicates the presence of the target nucleic acid sequence in the test sample.

In one embodiment, the methods and/or kits described herein may be used to amplify and detect a nucleic acid sequence that is associated with a particular organism or medical condition in a test sample. In one embodiment, the organism is a pathogenic organism, such as a bacteria or virus. In one embodiment, the virus is a double stranded DNA or RNA virus, or single stranded DNA or RNA virus. In one embodiment, the virus is an RNA virus or a DNA virus. In one embodiment, the test sample is a biological sample from a subject, such as a blood sample, sputum sample or nasopharyngeal sample, urine sample, feces sample or cerebrospinal fluid sample. In one embodiment, the biological sample is a tissue sample. Optionally, the subject is member of the animal kingdom. In one embodiment, the subject is a human. In one embodiment, the methods and kits described herein are useful for the clinical diagnosis of a medical condition, optionally a genetic condition or infectious disease. In one embodiment, the methods and/or kits described herein are useful for the diagnosis of critical infectious disease, such a disease caused by viral and/or bacterial pathogens.

In one embodiment, the test sample is an environmental sample, such as a water sample and the methods and/or kits described herein are for the detection of a particular organism in the environmental sample. In one embodiment, the organism is an infectious agent such as a virus, bacteria, or pathogen that contains a target nucleic acid sequence. In one embodiment, the target nucleic acid sequence is associated with a particular organism.

In one embodiment, the test sample is a foodstuff or other material susceptible to infection and/or contamination by an organism such as an infectious agent and the methods and/or its described herein are for the detection of a particular organism in the foodstuff or other material.

Yet another aspect provides a method of detecting the presence of a single nucleotide polymorphism (SNP) in a sample, comprising:

detecting the presence of a target nucleic acid sequence in a sample according the method described, wherein the recognition site recognized by the site-specific endonuclease comprises the SNP and the SNP is required for recognition of the recognition site by the site-specific endonuclease, and wherein detection of the amplified nucleic acid product indicates the presence of the SNP. Optionally, the SNP is a biomarker associated with a particular medical condition or disease.

Another aspect provides a method of detecting the methylation and/or hydroxymethylation status of a cytosine residue in a target sequence of a nucleic acid in sample, comprising:

detecting the presence of a target nucleic acid sequence in a sample according to the method described, wherein the recognition site recognized by the site-specific endonuclease comprises the cytosine residue, wherein the site-specific endonuclease is a methylation/hydroxymethylation sensitive endonuclease such that the endonuclease will not recognize the recognition site if the cytosine residue is methylated/hydroxymethylated, and wherein detection of the amplified nucleic acid product indicates the absence of methylation at the cytosine residue.

Yet another aspect provides a method of determining the zygosity of an allele in a sample from an organism, comprising:

e) detecting the presence of a target nucleic acid sequence in a sample according the methods described, wherein the target nucleic acid sequence is present in the allele, f) detecting the presence of the target nucleic acid sequence in a control sample according the methods described, wherein the zygosity of the allele in the control sample is known, and g) comparing the amount of amplified nucleic acid product detected in step a) and step b), and determining the zygosity of the allele in the sample based on said comparing.

In an embodiment the organism is a diploid, and:
an increased amount of amplified nucleic acid product detected in step a) relative to step b) indicates a homozygosity if the control sample is heterozygous;
a decreased amount of amplified nucleic acid product detected in step a) relative to step b) indicates a heterozygosity if the control sample is homozygous; and
an approximately equal amount of amplified nucleic acid product detected in step a) relative to step b) indicates the sample has the same zygosity as the control.

Another aspect provides a method of determining the ploidy state of a chromosome in a an organism, comprising:

h) detecting the presence of a target nucleic acid sequence in a sample according to the methods described, wherein the target nucleic acid sequence is a marker for the chromosome, i) detecting the presence of the target nucleic acid sequence in a control sample according to the methods described, wherein the ploidy of the chromosome in the control sample is known, and j) comparing the amount of amplified nucleic acid product detected in step a) and step b), and determining the ploidy of the chromosome in the sample.

In another aspect, there is provided a kit for detecting a target nucleic acid sequence in a sample according to the methods described herein. In one embodiment, the sample is a test sample from a subject. IN one embodiment, there is provided a kit for detecting a target nucleic acid sequence, wherein the target nucleic acid sequence comprises a recognition site recognized by a site-specific endonuclease, and the kit comprises:

a) a linear nucleic acid guidance primer, and
b) a circular DNA probe, wherein the guidance primer comprises a sequence complementary to the sequence of the recognition site, and wherein the circular DNA probe, comprises a sequence complementary to the sequence of the target nucleic acid, immediately upstream of the endonuclease cleavage site.

In an embodiment the described kits further comprise a DNA polymerase, optionally with strand displacement activity.

In one embodiment, the kit further comprises a site specific endonuclease. In one embodiment, the site specific endonuclease recognizes the recognition site in the target nucleic acid sequence. In one embodiment, the site specific endonuclease is a restriction endonuclease and/or a riboendonuclease.

In yet another embodiment the described kits further comprise a restriction pyrophosphatase.

In an embodiment the guidance primer is from 8 to 60 nucleotides in length, optionally from 12 to 20 nucleotides.

In an embodiment, the circular DNA probe is at least 20 nucleotides in length, optionally between 20 and 1000 nucleotides in length, between about 30 and 500 nucleotides in length, less than 300 nucleotides, less than 200 nucleotides or less than 100 nucleotides in length. In one embodiment, the circular DNA probe has a region that is complementary to at least 10, at least 12, at least 15 or at least 20 nucleotides at the 3' end of an initiation strand generated by cleavage of the nucleic acid substrate comprising the target nucleic acid sequence.

BRIEF DESCRIPTION OF THE DRAWINGS

One or more embodiments of the present disclosure will now be described in relation to the drawings in which:

FIG. 9A shows a guidance primer hybridizing to a denatured dsDNA template and that hybrids are suitable substrates for site specific endonuclease cleavage of the target strand. Following cleavage, the cleaved guidance primer fragments dissociate from the cleaved target strand. FIG. 9B shows the cleaved guidance primer fragment (generated upstream of the cleavage site) hybridizing to a circular DNA probe and priming a rolling circle amplification.

FIG. 10A shows different diluted fractions of M13(+) genomic DNA that have been contacted with a guidance primer and digested using AluI. FIG. 10B shows different diluted fractions of the digested products that have been contacted with a circular DNA probe and subjected to rolling circle amplification.

DETAILED DESCRIPTION

Figure 1:
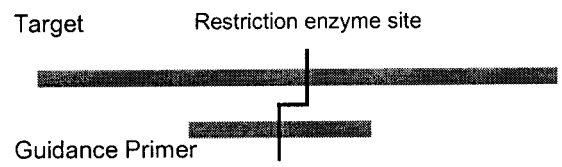
FIG. 1 is a schematic diagram representing the complementary base pairing association of a nucleic acid sequence, for example a single stranded DNA target, to the guidance primer, so as to create a suitable restriction endonuclease recognition site (⌐). Optionally, the guidance primer possesses suitably blocked 5' and 3' ends so as not to participate in any DNA polymerase mediated extension reactions. Step 2 shows that the cleavage of the guidance primer effectively yields digested strands that will spontaneously dissociate from the now cleaved target DNA. The target DNA, now suitably cleaved, produced a free 3-hydroxyl strand. Step 3 shows the newly produced cleavage product can specifically hybridize to the circular take-off probe by complementary base pairing. Step 4 shows the free 3'-hyroxy end on the target, resulting from the targeted endonuclease cleavage, can now prime the initiation of DNA synthesis by a rolling circle mechanism in the presence of a suitable DNA polymerase and trinucleotide phosphates, under suitable conditions.
Figure 1:
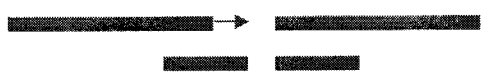
Figure 1:
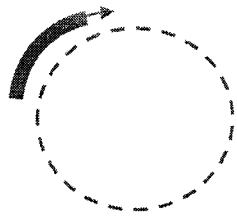
Figure 1:
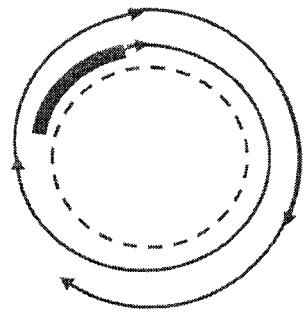

Other features and advantages of the disclosure will become apparent from the following detailed description. It should be understood, however, that the description and the specific examples while indicating preferred embodiments are given by way of illustration only, since various changes and modifications within the spirit and scope of the disclosure will become apparent to those skilled in the art from this description of various embodiments.

I. Definitions

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

As used herein, the singular forms "a", "an", and "the" include plural reference unless the context clearly dictates otherwise. As well, the terms "a" (or "an"), "one or more" and "at least one" can be used interchangeably herein.

The term "nucleic acid" or "nucleic acid molecule" as used herein refers to a sequence of nucleotide or nucleoside monomers consisting of naturally occurring bases including modified bases, sugars, and inter-sugar (backbone) linkages, and is intended to include DNA, RNA, and combinations thereof, and which can be either double stranded or single stranded, and may represent the sense or antisense strand.

The term "endonuclease" refers to an enzyme capable of cleaving one or both strands of a nucleic acid, including DNA, RNA, or combinations thereof. A "site-specific endonuclease" refers to an endonuclease which cleaves a nucleic acid at or near specific recognition sites. A "recognition site" for a site-specific endonuclease may be a single stranded and/or double stranded nucleic acid sequence, or may be a structural motif that is capable of conferring sequence specificity. Site-specific endonucleases which cleave nucleic acid at or near a specific nucleotide sequence are well known in the art, including for example, restriction enzymes. Site-specific endonucleases as described herein are not limited to endonucleases having native sequence specificity, and include endonuclease that have specificity for a structural motif that is capable of conferring sequence specificity. For example, Ribonuclease H (RNase H) has site-specificity for of cleaving the RNA strand of a DNA-RNA hybrid to yield a 3'-hydroxyl and a 5'-phosphate at the hydrolysis site. Hybridizing a synthetic primer comprising RNA bases to a single stranded DNA strand, can confer sequence specificity to RNase H. A number of structural motif that are capable of conferring sequence specificity to an endonuclease are known in the art, and include, for example flap endonucleases and riboendonucleases such as Dicer.

The term "restriction endonuclease" as used herein refers to an enzyme that is capable of cleaving a nucleic acid at or near a restriction site. The term "restriction site" as used herein refers to a nucleic acid sequence which is recognized by a restriction enzyme. A large number of restriction endonucleases and their associated restriction sites are known in the art. A non-limiting example of a restriction enzyme is EcoRI which recognizes the restriction site GAATTC on double stranded DNA and cuts between the G and the A on both strands.

The term "nucleic acid substrate" as used herein refers to a nucleic acid that is capable of being cleaved by a specified endonuclease, including a site-specific endonuclease. The nucleic acid substrate may be double stranded, single stranded, or a combination thereof. In one embodiment, the nucleic acid substrate is a chromosome. In one embodiment, the nucleic acid substrate is viral DNA. In one embodiment, the nucleic acid substrate comprises a target sequence that is to be amplified and optionally detected using the methods and/or kits described herein. In one embodiment, the target sequence includes a recognition site recognized by a site-specific endonuclease. In one embodiment, the target sequence is a nucleic acid sequence from a specific organism that comprises a recognition site recognized by a site-specific endonuclease. In one embodiment, the target sequence is a nucleic acid sequence selected to have a recognition site recognized by a site-specific endonuclease and is a sequence that is associated with a medical condition. For example, in one embodiment, the target sequence is associated with a particular disease, pathogen or genetic condition.

The term "initiation strand" refers to a single stranded nucleic acid. In certain embodiments the initiation strand may be a naturally occurring nucleic acid or derived therefrom as fragment thereof, or as an amplification product of a naturally occurring nucleic acid sequence or fragment thereof. In one embodiment, the initiation strand comprises a recognition site for a site specific endonuclease, or the complement of a recognition site for a site specific endonuclease. In one embodiment, the initiation strand comprises a sequence upstream of a recognition site that is complementary to a sequence on a circular DNA probe such that cleavage of the initiation strand by the site specific endonuclease allows the upstream cleavage product to hybridize to a circular DNA probe as described herein and serve to prime rolling circle amplification. In some embodiments, the initiation strand is at least 15 nucleotides, at least 18 nucleotides, at least 20 nucleotides, at least 30 nucleotides, at least 50 nucleotides, at least 100 nucleotides, at least 500 nucleotides, at least 1000 nucleotides, or at least 5000 nucleotides. In one embodiment, the initiation strand comprises a single stranded chromosome or a fragment of a single stranded chromosome.

The term "primer" as used herein refers to a nucleic acid sequence, whether occurring naturally as in a purified restriction digest or produced synthetically, with a 3' hydroxyl end that is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. In one embodiment, the cleavage product that is the result of a site specific endonuclease cleaving an initiation strand hybridizes to a complementary region on a circular DNA probe and acts as a primer for rolling circle amplification of the circular DNA probe.

In one embodiment, the initiation strand comprises a sequence upstream of the recognition site that is complementary to a sequence on a circular DNA probe. In one embodiment, the complementary sequence is at least 10 nucleotides, at least 12 nucleotides, at least 15 nucleotides, at least 18 nucleotides or at least 20 nucleotides. In one embodiment, the complementary sequence is between about 10 nucleotides and 50 nucleotides, between about 12 nucleotides and 40 nucleotides or between about 15 nucleotides and 30 nucleotides.

The term "guidance primer" refers to a primer which is complementary to a pre-determined region within a single stranded target nucleic acid. The guidance primer may be used to render the single stranded target nucleic acid competent for cleavage by a site-specific endonuclease, for example by generating a double stranded restriction site recognized by a restriction enzyme. The guidance primer may be a non-naturally occurring and/or synthetic nucleic acid. In one embodiment, the 5' and/or 3' ends of the guidance primer may be modified to prevent their use as primers. In one embodiment, the 3' end of the guidance primer is modified to prevent extension of the nucleic acid by a polymerase. For example, in one embodiment, non-specific extension from the guidance primer is prevented by blocking with dideoxynucleotides or phosphothioate modified 5' and 3' ends. In one embodiment, this renders the guidance primer inert until it is specifically cleaved by the desired restriction endonuclease following hybridization to its corresponding target region. This enables the guidance primer to be present in reasonably high concentrations, to drive rapid hybridization to a specific target, but not interfere with the reaction in a negative manner. In one embodiment, the guidance primer does not hybridize to the circular DNA probe or serve as a primer for rolling circle amplification. In one embodiment, modifying the 5' and/or 3' ends helps prevent exonuclease degradation of the guidance primer and renders the methods and/or kits described herein more resistant to the presence of exonucleases in samples and/or test samples.

The term "amplification primer" as used herein, refers to a primer that may be used to enhance the sensitivity of the site-specific endonuclease guided rolling circle amplification. For example, an amplification primer may be a primer having an identical sequence to a region of the circular DNA probe, such that the amplification primer is capable of hybridizing to each concatenated repeat of the amplification product and priming further amplification.

The term "circular DNA probe" and "take-off probe" are used interchangeably herein and refer to a single stranded covalently closed circular DNA molecule. The circular DNA probe may have a nucleic acid sequence that is complementary to a region immediately upstream of an endonuclease recognition site on a target nucleic acid substrate. In one embodiment, the circular DNA probe has a sequence that is complementary to the upstream 3' end of a cleavage product of an initiation strand contacted with a site specific endonuclease. Optionally, the circular DNA probe may be less than 40 nucleotides, about 40 nucleotides, between 40-120 nucleotides, between 50 and 100 nucleotides, between 30 and 60 nucleotides or greater than 120 nucleotides. In some embodiments, the circular DNA probe may include elements such as a duplex forming region enabling post-transcription restriction endonuclease digestion for resolving the concatenated transcription products, or promoting the binding of a double stranded DNA binding dye for detection. Alternatively, and/or in addition the circular DNA probe may include specific complementary regions can be designed to foster hybridization to detection probes, other desirable sequences which may enable hybridization of the transcription products to an array or suitable complement for decoding in a multiplexed reaction.

The term "primed" or "priming" as used herein refers to the act of a nucleic acid molecule with a free 3' hydroxyl group acting as an initiation point for template guided synthesis of a primer extension product.

The term "3' hydroxyl end" refers to the end of a nucleic acid chain which terminates at a free hydroxyl group of the third carbon in the sugar-ring.

The term "nucleic acid amplification" refers to a process of nucleic acid synthesis generating multiple copies of a nucleic acid sequence.

The term "rolling circle amplification" or "RCA" refers to a unidirectional nucleic acid amplification process by which a target with a free 3' hydroxyl end is used to prime a DNA synthesis reaction, such as by using a DNA polymerase, resulting in concatenated extension products as the synthesized strand is repeatedly displaced and extended around a circular template. In one embodiment, generating an amplified nucleic acid product by RCA comprises contacting a circular DNA probe and primer with dNTPs and a polymerase enzyme. In one embodiment, the primer is the upstream cleavage product of an initiation strand or nucleic acid substrate cleaved with an site specific endonuclease.

The term "complementary" as used herein refers to the capacity of nucleotides to associate through hydrogen bonding to form double stranded nucleic acid molecules. The following base pairs are related by complementarity: guanine and cytosine; adenine and thymine; and adenine and uracil. The region of complementarity between two nucleic acid molecules refers to the sequence over which the two nucleic acid molecules are substantially fully base-paired when hybridized.

The term "denature" refers to the separation of double stranded nucleic acid into two single strands, by disruption of the hydrogen bonding between complementary strands. Nucleic acids may be denatured by thermal or chemical means known in the art, including for example, by adjusting pH, using a chemical denaturant such as urea, or by using an agent that chemically modifies the bases, such as reactive aldehydes.

The term "hybridize" refers to the sequence specific non-covalent binding interaction with a complementary nucleic acid. Appropriate stringency conditions which promote hybridization are known to those skilled in the art, or can be found in Current Protocols in Molecular Biology, John Wiley & Sons, N.Y. (1989), 6.3.1 6.3.6. In a preferred embodiment, the hybridization conditions are conditions under which the site specific endonuclease and/or the polymerase are active.

Optionally, in some embodiments, the initiation strand may be fixed to a membrane or other surface and hybridization of the initiation strand to the circular DNA probe includes a wash step to remove unspecifically bound probe. The stringency may be selected based on the conditions used in the wash step. For example, the salt concentration in the wash step can be selected from a high stringency of about 0.2×SSC at 50° C. for 15 minutes. In addition, the temperature in the wash step can be at high stringency conditions, at about 65° C. for 15 minutes. In other embodiments, the methods described herein may be performed without a wash step.

In one embodiment, the methods described herein involve hybridizing the nucleic acid substrate, initiation strand, guidance primer and/or circular DNA probe under moderately stringent hybridization conditions. By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 10, 12, 15 or greater than 15 (e.g. 20, 25, 30, 40 or 50) nucleotides in length. In one embodiment, hybridization occurs between a target nucleic acid molecule comprising a recognition site and a guidance primer. In one embodiment, hybridization occurs between the 3' end region immediately upstream of the recognition site and a circular DNA probe.

Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, in some embodiments, the parameters that determine hybrid stability are sodium ion concentration and temperature. Based on these considerations those skilled in the art will be able to readily select appropriate hybridization conditions. By way of example, the following conditions may be employed to achieve stringent hybridization between a nucleic acid molecule attached to a surface and a nucleic acid molecule in solution: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. for 15 minutes. Moderately stringent hybridization conditions include a washing step in 3×SSC at 42° C. for 15 minutes. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

In one embodiment, the hybridization conditions are selected based on the desired specificity and stringency of the hybridization. In one embodiment, hybridization conditions are selected to encourage the binding of a guidance primer to a nucleic acid substrate, and/or the binding of an initiation strand to a circular DNA probe as described herein. A skilled person will appreciate that by modifying the temperature and/or chemical composition of the hybridization solution, for example by increasing or decreasing the hybridization temperature, it is possible modulate the specificity and stringency of the hybridization. Optionally, the hybridization conditions are modified by the addition of other ligands to control or modulate hybridization. In one embodiment, the hybridization conditions are conditions under which the site-specific endonuclease and/or polymerase enzymes are active. In one embodiment, the hybridization conditions include a temperature between about 15 degrees Celsius and 45 degrees Celsius, between about 15 degrees Celsius and 70 degrees Celsius, between about 20 degrees Celsius and 65 degrees Celsius. In one embodiment, the hybridization temperature is less than about 70 degrees Celsius, less than about 65 degrees Celsius, less than about 60 degrees Celsius or less than about 40 degrees Celsius. In one embodiment, the temperature of the hybridization is an ambient temperature.

As used herein, an "ambient temperature" refers to the temperature of the surroundings. The ambient temperature may be a temperature inside a temperature-controlled area or not. In one embodiment, the ambient temperature is between about 20 and 30 degrees Celsius, optionally between about 20 and 25 degrees Celsius.

The term "methylation and/or hydroxymethylation" as used herein refers to the process whereby a methyl group or hydroxymethyl group is added to a cytosine residue of a DNA molecule.

As used herein, a nucleic acid sequence that is "associated with a medical condition" refers to a nucleic acid sequence whose occurrence in a subject, more often than can be readily explained by chance, is observed with the medical condition in the subject. For example, a nucleic acid sequence encoding a cystic fibrosis transmembrane conductance regulator (CFTR) protein with a ΔF508 mutation is associated with the medical condition cystic fibrosis.

As used herein, a nucleic acid sequence that is "associated with an organism" refers to a nucleic acid sequence that is observed in the nucleic acids of a specific organism that is not observed in the nucleic acids of other organisms. In one embodiment, a nucleic acid sequence that is "associated with an organism" is a nucleic acid sequence that is unique to that organism.

II. Methods and Kits

The present disclosure is directed at methods of using site specific endonuclease enzymes to specifically target a nucleic acid sequence and generate an initiation strand with a 3' hydroxyl end that can then initiate a rolling circle reaction. The method may be used to detect the presence of target sequences in both single stranded and double stranded nucleic acid targets. Also provided are kits suitable for performing a method as described herein.

An aspect of the disclosure provides a method of nucleic acid amplification, comprising:
a) providing a sample comprising a nucleic acid substrate, wherein the substrate comprises a recognition site recognized by a site-specific endonuclease;
b) cleaving the substrate with the endonuclease;
c) contacting the cleaved substrate with a circular DNA probe under conditions that allow for hybridization between complementary sequences of the cleaved substrate and the circular DNA probe; and
d) generating an amplified nucleic acid product by rolling circle amplification (RCA).

In an embodiment, the RCA is primed by hybridization of a 3' region of the cleaved nucleic acid substrate to the circular DNA probe, wherein the 3' region comprises a free 3'-hydroxyl end generated upon cleavage of the substrate by the endonuclease In one embodiment, the recognition site is a single stranded nucleic acid sequence. In another embodiment, the recognition site is a double stranded nucleic acid sequence. In yet another embodiment, the double stranded recognition site of the substrate comprises double stranded DNA, double stranded RNA, a DNA:RNA hybrid duplex, or a combination thereof.

In an embodiment, step a) of the described methods comprises generating the nucleic acid substrate from a single stranded nucleic acid initiation strand. In yet another embodiment, the initiation strand is single stranded RNA, single stranded DNA, or a combination thereof.

The methods described herein may be used to initiate amplification and/or to detect a target sequences in both single and double stranded nucleic acids. For example, if the recognition site recognized by the site-specific endonuclease is a single stranded nucleic acid sequence, and the site specific endonuclease is capable of cleaving the single stranded nucleic acid, the methods can be use directly on the single stranded nucleic acid. Restriction enzymes that cleave single stranded DNA are known in the art, and include, for example, AvaII, HaeII, DdeI, AluI, Sau3AI, AccII, TthHB8I and HabII.

In certain applications, wherein the target is a single stranded nucleic acid (i.e. initiation strand) and the recognition site is a double stranded sequence, an additional step of generating a cleavage competent substrate from the initiation strand may be required. For example, a guidance primer may be used which is complementary to a pre-determined region within initiation strand to generate the double stranded recognition site.

In an embodiment, the guidance primer is designed in such a way that cleavage by the endonuclease produces two fragments of the guidance primer whose melting temperature is substantially lower than the primer in its entirety. In this way, once cleaved, the remaining primer fragments disassociate from the template. Such a guidance primer could be generated by a person skilled in the art. Typically the guidance primer is from 8 to 60 nucleotides in length, optionally from 12 to 20 nucleotides, or from 15 to 25 nucleotides.

Figure 9A:
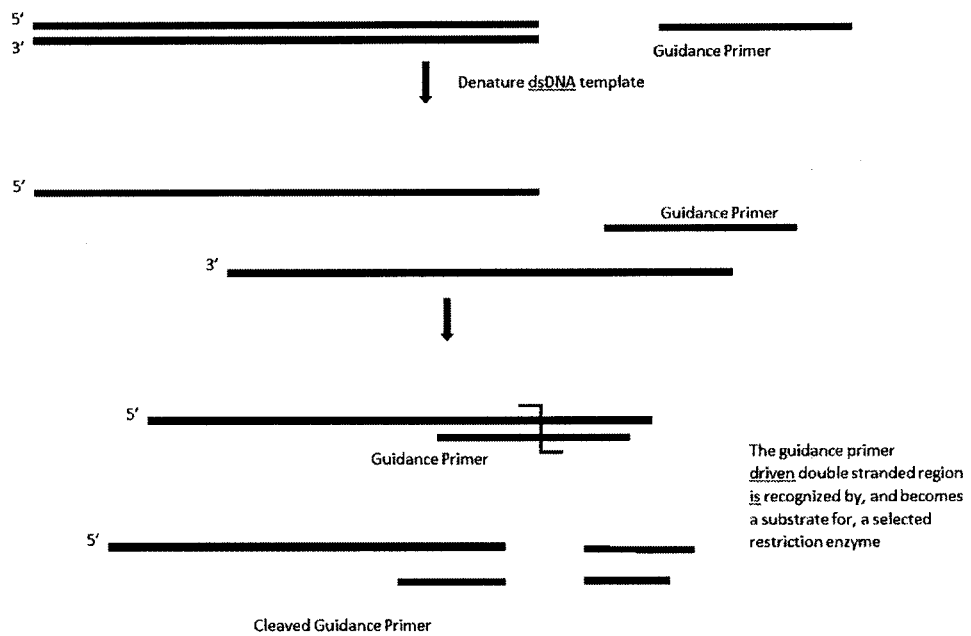
FIGS. 9A and 9B show the use of a guidance primer with double stranded templates.
Figure 9B:
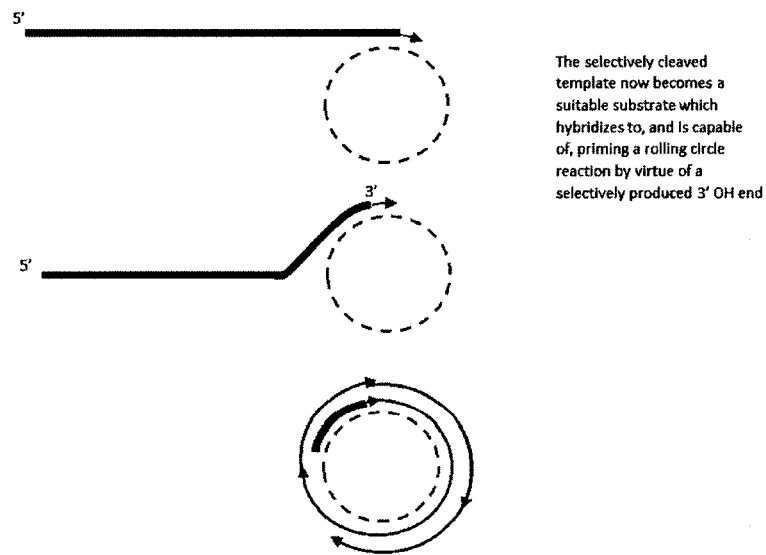

For example, as shown in FIG. 9 double stranded templates may be used in the methods described herein with a pre-selected restriction enzyme and suitably designed guidance primer and a covalently closed circularized primer. A person skilled in the art will recognize that suitable genomic regions can be chosen to react with one of a multitude of commercially available restriction enzymes. They include, but are not limited to palindromic, or non-palindromic, 4-6- or 8-base pair recognition sequences. Alternatively, enzymes which selectively cleave only one strand of a duplex DNA may be used in the methods and kits described herein. For example, in one embodiment the site specific endonuclease is a nicking restriction endonucleases, e.g., Nt.BspQI which recognizes the duplex sequence GCTCTTCN but can only cleave the top strand as follows:

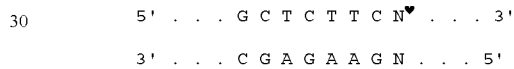

In one embodiment, the guidance primer will produce the recognition sequence on either a single stranded or originally denatured double stranded, but it itself is not cleaved. In one embodiment, the cleaved genomic sequence becomes a suitable substrate for hybridizing to a complementary circle primer and initiating the rolling circle reaction. Alternatively, restriction enzymes which recognize a palindromic, or non-palindromic, sequence, but cleave a distance away from the recognition sequence can be used, for example BceAI (ACGGC(12/14)) or homing enzymes.

Alkali or heat denatured DNA, when exposed to a suitable, sequence specific guidance primer creates a double stranded hybrid elevating the necessity for all the genomic DNA to re-hybridize. This can act to further confer selectivity and specificity of the amplification reaction as unhybridized genomic DNA (without a sequence specific guidance primer hybridized) will not act as a suitable substrate for the chosen restriction enzyme. In one embodiment, this enables the guidance primer to selectively and specifically hybridize to the chosen sequence(s) even in complex matrix types (i.e., blood, stool, etc).

In one embodiment, the nucleic acid substrate (single stranded or double stranded) is then contacted with a site specific endonuclease in order to generate a cleavage product that can hybridize to the circular DNA probe and prime rolling circle amplification.

The initiation strand, which is specifically cleaved, can hybridize to the circular DNA probe (also referred to as the "take-off probe") which is complementary to the 3' end of the initiation strand generated by cleavage. The take-off probe is composed of circularized DNA, which when hybridizing to the cognate initiation strand, will enable the initiation of a rolling circle amplification (RCA) in the presence of a DNA polymerase. By selecting appropriate restriction endonuclease restriction sites, which produce a suitable free-3'-hyroxyl end, take-off probe hybridization can occur at pre-destined regions suitable for amplification. DNA polymerases suitable for RCA are known in the art, including, for example, DNA polymerases phi29 DNA Polymerase and Bst DNA polymerase as demonstrated in Example 7.

In another embodiment, the double stranded recognition site of the substrate can be generated from the initiation strand by synthesizing a complementary strand using the initiation strand as template. Methods of complementary strand synthesis using primer extensions are known in the art, including synthesis using a DNA polymerase, DNA-dependent RNA polymerase, RNA-dependent RNA polymerase, or a reverse transcriptase.

A chosen restriction enzyme may potentially produce multiple cleavage sites which can be used in conjunction with multiple guidance-primer sequences to initiate multiplexed amplification of one or multiple target sequences. In this embodiment, the presence of a target nucleotide sequence can be assessed by the presence of amplification product, which would be desirable if the test were designed to detect, for example, a pathogenic or infectious agent. The use of multiplexed amplification may also act to increase sensitivity and enable detection of lower target loads.

In an embodiment, the rolling circle amplification is linear rolling circle amplification. Linear RCA may, for example, be used in applications where accurate quantification of the target sequence is desired.

In an embodiment, the rolling circle amplification occurs in the presence of an amplification primer, wherein the amplification primer is a nucleic acid molecule comprising a sequence at the 3' end of the amplification primer which is complementary to a sequence of the amplified nucleic acid product.

Use of an amplification primer may be preferred in applications, for example, where enhanced sensitivity is desired. For example, an amplification primer may be a primer having an identical sequence to a region of the circular DNA probe, such that the amplification primer is capable of hybridizing to each concatenated repeat of the amplification product and priming further amplification. In one embodiment, RCA produces a concatenated ssDNA product. Optionally, the methods and kits described herein include the use of an amplification primer used to generate dsDNA. In one embodiment, the methods and kits include the use of a ligase to join adjacent fragments complementary to the amplified nucleic acid product synthesized starting from the amplification primer off of the ssDNA transcription product. In some embodiments, additional primers may be selected to further geometric or exponential amplification once the rolling circle reaction has started.

In both linear RCA and methods using the amplification primer, a person skilled in the art would be able to assess the linear range of the amplification reaction by performing a matrix type experiment whereby the target, take-off probe and enhanced amplification primer would be sequentially diluted in a reaction to assess the limits of each reaction component. For example, holding the take-off primer and enhanced amplification primer constant, the target would be sequentially diluted to establish the linear range. Subsequently within this range, the take-off probe would be sequentially diluted to establish the best performing range and finally, the enhanced amplification primer would be added in decreasing concentrations to establish the optimal working range. The absolute linear range may be different for each primer design and likewise, for each target, as the sequence variability may influence the range covered, but generally the parameters will bracket a particular concentration of take-off primer and enhanced amplification primer (if used).

The use of one or more circular DNA probes may also be used to identify the presence of multiple target sequences in a single reaction, for example, by using differently labeled probes which bind to amplification products from different circular DNA probes.

It will be appreciated that the described methods may also be used with single stranded RNA or DNA molecules. Where RNA is used as the single stranded template, direct binding of the guidance primer to the RNA will generate an RNA:DNA heteroduplex, which may be cleaved by restriction endonucleases which are capable of cleaving heteroduplex DNA. For example, the restriction enzymes AvaII, AvrII, BanI, HaeIII, HinfI and TaqI are known to be able to recognize and cleave restriction sites in DNA-RNA heteroduplex. As already described, RNase H may also be used to selectively cleave DNA-RNA heteroduplex.

In another embodiment, a complementary DNA (cDNA) target can be generated by a reverse transcriptase reaction to produce a DNA-RNA heteroduplex, or a DNA single stranded template by treating with RNase or using a reverse transcriptase with RNase activity. A single stranded cDNA target created in this way can be hybridized by the guidance primer and acted upon by a suitable site-specific endonuclease to generate a suitable free-3'-hyroxyl end capable of hybridizing to the take-off probe and initiating RCA.

In another embodiment, endogenous endonuclease processing may be used as the source of the site-specific endonuclease. For example, a single stranded RNA molecule may be endogenously processed by cellular processes, for example, a processed microRNA. In an embodiment, pre-processed RNA targets could bind the take-off probe, and be endogenously processed to generate the required free 3' end to initiate extension.

Single stranded RNA may also be processed exogenously by an added riboendonuclease to generate a free-3'-hyroxyl end for rolling circle initiation.

In an embodiment, a double stranded DNA substrate can be acted upon by a chosen site-specific endonuclease to generate a suitable cleaved fragment. In an embodiment, the cleaved DNA can be rendered single stranded by thermal or chemical denaturation. Competitive binding could allow the take-off probe to bind to one or both of the dissociated strands. In another embodiment, post cleavage, hybridizing of the take-off probe can be allowed to occur at uniform temperature through mass action under isothermal conditions.

It will be appreciated that the methods described herein may be carried out under isothermal conditions and in a single reaction as described in Example 6. A skilled person would be able to select appropriate buffer conditions which would allow both the endonuclease and polymerase to function in the same reaction.

Numerous methods of detecting amplified nucleic acid products are generally known in the art, including detection in situ, in gel via electrophoresis, in a lateral flow, in microarray, and/or on a bead surface. For example, in situ detection can be accomplished by labeling of the amplified nucleic acid product, for example using fluorescent labeled nucleotides, hapten labeled nucleotides, fluorescent labeled probes, molecular beacons, fluorescent barcodes and/or fluorescent DNA binding dyes.

It will be appreciated that the fluorescent DNA binding dye may be a single strand specific fluorescent DNA binding dye or a double strand specific fluorescent DNA binding dye.

In an embodiment, the generation of amplified product is detected in situ in real time, for example, using single strand DNA binding dye, such as SYBR green. Other dyes for binding single and double stranded DNA are well known in the art.

In another embodiment, the disclosed methods may be used to assess the methylation status of a DNA sequence by using a methylation sensitive site-specific endonucleases. Numerous methylation sensitive restriction enzymes are known in the art, including, for example, Aat II, Acc II, Aor13H I, Aor51H I, BspT104 I, BssH II, Cfr10I, Cla I, Cpo I, Eco52, Hae II, Hap II, Hha I, Mlu I, Nae I, Not I, Nru I, Nsb I, PmaC I, Psp1406 I, Pvu I, Sac 11, Sal I, Sma I, and SnaB I. Using a methylation sensitive restriction enzyme, cleavage would only occur in the absence of methylation at the recognition site, so that production of an amplification product would be indicative of a lack of methylation.

In one embodiment, the methods and kits described herein may be used to amplify and detect a target nucleic acid sequence. In some embodiments, the target nucleic acid sequence may be a nucleic acid sequence associated with an organism, such as a pathogenic organism, or a medical condition.

Nucleic acid sequences that are associated with a particular medical condition are well known in the art. For example, nucleic acid variants, such as SNPs and/or other mutations, have been associated with a number of medical conditions in humans, including, but not limited to, those described in Online Mendelian Inheritance in Man (OMIM) available at (http://www.omim.org/). A skilled person would readily be able to practice the methods as described herein by identifying a restriction site within or adjacent to a nucleic acid variant that has been associated with a medical condition and synthesizing a circular DNA probe containing a sequence that is complementary to the sequence generated by cleaving the initiation strand with the site specific endonuclease as described herein.

Furthermore, a skilled person would also readily be able to identify nucleic acid sequences that are associated with a particular medical condition organism, by using bioinformatic tools and publically available nucleic acid sequence databases. For example, sequences that are associated with a particular organism and do not appear in the nucleic acid sequences of other organisms may be identified by using bioinformatics tools such as nucleotide BLAST (Basic Local Alignment Search Tool), maintained by the National Center for Biotechnology Information, National Library of Medicine, Bethesda, Md.

It will be appreciated that the presence of single nucleotide polymorphisms (SNPs) within a target site can be assessed by the disclosed methods, by choosing suitable site-specific endonucleases which is sensitive to the presence of the recognition site recognized by the site-specific endonuclease. For example, a restriction enzyme can be chosen that will only cleave substrate nucleic acid if the SNP is present. If the SNP is present, RCA will proceed following complementary base pairing of the cleaved target to the take-off probe. Accordingly, the generation of the amplified nucleic acid product would indicate the presence of the SNP. In some embodiments, the methods and kits disclosed herein are useful for genetic testing of a sample from a subject for the presence or absence of a particular SNP. In some embodiments, the SNP is associated with or indicative of a medical condition or disease.

In another embodiment, the sample comprises nucleic acid from a naturally occurring source, for example, genomic DNA, plasmid, or viral sequences. The methods described herein may be used to detect the presence of a naturally occurring viruses and/or pathogens. Where the sample comprises naturally occurring nucleic acid, in an embodiment, the RCA is primed by a cleavage product derived from the naturally occurring strand. It is contemplated that the use of a strand derived from the sample, rather than the strand derived from the guidance primer, may be beneficial to reduce false positive results.

For example, in one embodiment, the methods and/or kits described herein may be used to amplify and detect a nucleic acid sequence that is indicative of a particular organism or is associated with a particular medical condition or disease in a test sample. In one embodiment, the organism is a pathogenic organism. In one embodiment, the test sample is a biological sample from a subject, such as a blood sample or tissue sample. In one embodiment, the test sample is a sample from a subject that contains a detectable amount of nucleic acid molecules. In one embodiment, the methods and kits described herein are useful for the clinical diagnosis of a medical condition or disease, optionally a genetic condition or infectious disease or pathogen. In one embodiment, the sample is from a subject having or suspected of having a medical condition or infectious disease.

For example, in one embodiment the methods and/or kits described herein may be used to test for nucleic acid variants associated with medical conditions or diseases including, but not limited to, cancer, heart disease or diabetes or nucleic acids variants associated with genetic conditions or diseases including, but not limited to cystic fibrosis, sickle cell disease, Fragile X syndrome, muscular dystrophy, or Huntington disease.

The methods and kits described herein may also be used to detect a target nucleic acid sequence in an environmental sample, such as a water sample. In one embodiment, the test sample is an environmental sample and the methods and/or kits described herein are for the detection of an organism or infectious agent, such as a virus, bacteria, other organism or pathogen, in the environmental sample.

In another embodiment, the methods and kits described herein may be used to detect a target nucleic acid in a foodstuff or other material susceptible to infection and/or contamination by infectious agents such as a viruse, bacteria and/or fungus. In one embodiment, the test sample is a sample of a foodstuff or other material and the presence of the target nucleic acid in the test sample is indicative of the infectious agent in the foodstuff or other material.

An aspect provides a method of determining the zygosity of an allele in a sample from an organism, comprising:

e) detecting the presence of a target nucleic acid sequence in a sample according the methods described, wherein the target nucleic acid sequence is present in the allele, f) detecting the presence of the target nucleic acid sequence in a control sample according the methods described, wherein the zygosity of the allele in the control sample is known, and g) comparing the amount of amplified nucleic acid product detected in step a) and step b), and determining the zygosity of the allele in the sample based on said comparing.

It will be appreciated that methods of determining zygosity are conducted within the linear range of the amplification reaction, which may be assessed by a skilled person, as described above.

In an embodiment the organism is a diploid, and:
an increased amount of amplified nucleic acid product detected in step a) relative to step b) indicates a homozygosity if the control sample is heterozygous;

a decreased amount of amplified nucleic acid product detected in step a) relative to step b) indicates a heterozygosity if the control sample is homozygous; and an approximately equal amount of amplified nucleic acid product detected in step a) relative to step b) indicates the sample has the same zygosity as the control.

Another aspect provides a method of determining the ploidy state of a chromosome in a an organism, comprising:

h) detecting the presence of a target nucleic acid sequence in a sample according to the methods described, wherein the target nucleic acid sequence is a marker for the chromosome, i) detecting the presence of the target nucleic acid sequence in a control sample according to the methods described, wherein the ploidy of the chromosome in the control sample is known, and j) comparing the amount of amplified nucleic acid product detected in step a) and step b), and determining the ploidy of the chromosome in the sample.

It will be appreciated that methods of determining ploidy are conducted within the linear range of the amplification reaction, which may be assessed by a skilled person, as described above.

Yet another aspect provides a kit for amplifying a target nucleic acid sequence as described herein. In one embodiment, the target nucleic acid sequence comprises a recognition site recognized by a site-specific endonuclease. In one embodiment, the kit comprises:

a) a linear nucleic acid guidance primer, and
b) a circular DNA probe, wherein the guidance primer comprises a sequence complementary to the sequence of the recognition site,
and wherein the circular DNA probe, comprises a sequence complementary to the sequence of the target nucleic acid, immediately upstream of the endonuclease cleavage site.

An aspect of the disclosure provides a kit for detecting a target nucleic acid sequence, wherein the target nucleic acid sequence comprises a recognition site recognized by a site-specific endonuclease. In one embodiment, the kit comprises:

c) a linear nucleic acid guidance primer, and
d) a circular DNA probe, wherein the guidance primer comprises a sequence complementary to the sequence of the recognition site,
and wherein the circular DNA probe, comprises a sequence complementary to the sequence of the target nucleic acid, immediately upstream of the endonuclease cleavage site.

In an embodiment the described kits further comprise a DNA polymerase, optionally with strand displacement activity. In an embodiment the polymerase is Phi29 DNA polymerase and/or Bst DNA polymerase.

In another embodiment the described kits further comprise restriction endonuclease and/or a riboendonuclease.

In yet another embodiment the described kits further comprise a pyrophosphatase.

In yet another embodiment the described kits further comprise one or more detection reagents, optionally labeled probes, molecular beacons, fluorescent barcodes and/or fluorescent DNA binding dyes, optionally strand specific fluorescent DNA binding dye or a double strand specific fluorescent DNA binding dye.

In an embodiment the described kits contain buffer, which is optimized to allow both polymerase and endonuclease reactions to proceed in a single reaction.

In an embodiment the guidance primer is from 8 to 60 nucleotides in length, optionally from 12 to 20 nucleotides. In one embodiment, the sequence of the guidance primer is complementary to the target nucleic acid sequence upstream, downstream or both upstream and downstream of the recognition site. For example, in some embodiments, the guidance primer is complementary to the recognition site and at least 10, at least 12, at least 15 or greater than 15 nucleotides upstream, downstream or a combination thereof, of the recognition site.

In one embodiment, the circular DNA probe is at least 20 nucleotides in length, optionally between 30 and 500 nucleotides in length. In one embodiment, the circular DNA probe may comprise additional sequence elements, such as, but not limited to, a duplex forming region enabling post-transcription restriction endonuclease digestion. In one embodiment, the circular DNA probe comprises a sequence complementary to the sequence of the target nucleic acid at least 10, at least 12 or at least 15 nucleotides in length.

In an embodiment the target nucleic acid sequence is a sequence associated with or indicative of a medical condition or organism, such as a genetic disorder or an infectious agent. In an embodiment the a target nucleic acid sequence is a sequence associated with Pneumonia, Meningitis, dengue, Fever and Rash illness, sepsis, Malaria, Hospital Acquired Infections, Sexually transmitted diseases and/or respiratory illnesses.

In another embodiment the a target nucleic acid sequence is a sequence associated with *Mycoplasma* pneumonia, *Chlamydophilla* pneumonia, *Legionella* pneumonia, Enterovirus 71, *Streptococcus suis*, *Neisseria meningitides*, Dengue virus 1-4, Coxsackie virus, *Plasmodium viridae*, *Staphylococcus aureus*, *Enterobacteriaciae*, *Enterococcus* spp, and/or Human Parvovirus.

The kits may further comprise instructions and/or additional reagents known in the art.

The following non-limiting examples are illustrative of the present disclosure:

EXAMPLES

Example 1: Synthesis of Guidance Primer and M13 Template Mimetic

A linear, 17 base, nucleic acid oligonucleotide designated the guidance primer (SEQ ID NO: 1) was designed and purchased from ACTG Corp (Toronto, Ontario) so as to be complementary (POSITIVE POLARITY) to a region of the single stranded (NEGATIVE POLARITY) bacteriophage M13 sequence. SEQ ID NO: 1 contains the restriction endonuclease recognition sequence Alu1, as shown underlined.

```
>M13-frag#1-Alu1-3'(+)
                                    SEQ ID NO: 1
CGTTTGAAGCTCGAATT
```

A synthetic mimetic of the M13 single stranded (NEGATIVE POLARITY) bacteriophage M13 sequence (SEQ ID NO: 2), was ordered from ACGT Corporation (Toronto, Ontario), to permit testing of the invention, and is represented by the sequence. The Alu1 restriction endonuclease site is indicated by underlining.

```
>M13frag#1(-)target
                                    (SEQ ID NO: 2)
ATTAAGAGGAAGCCCGAAAGACTTCAAATATCGCGTTTtAATTCGAGCTT

CAAAGCGAA
```

Example #2: Production of Circularized Take-Off Probe

A circularizable sequence, represented by SEQ ID NO: 3, containing a 5' phosphate modification, capable of ligating to the 3'-hydroxyl in a desirable intramolecular reaction mediated by CircLigase™ ssDNA Ligase (Epicentre® Biotechnologies, Madison, Wis.) was designed. The sequence was circularized with the CircLigase enzyme and covalently closed circles were purified from linear forms by treatment of the reaction with Exonuclease I and Exonuclease III.

```
>M13(+)Replicircle#3
                                    SEQ ID NO: 3
PO4-CTCGAATTaAAACGCGATATTTGAAGTCTTTCGGGCTTCCTCT-
OH
```

Example #3: AluI Restriction Digestion of Mimetic Target

Figure 2:
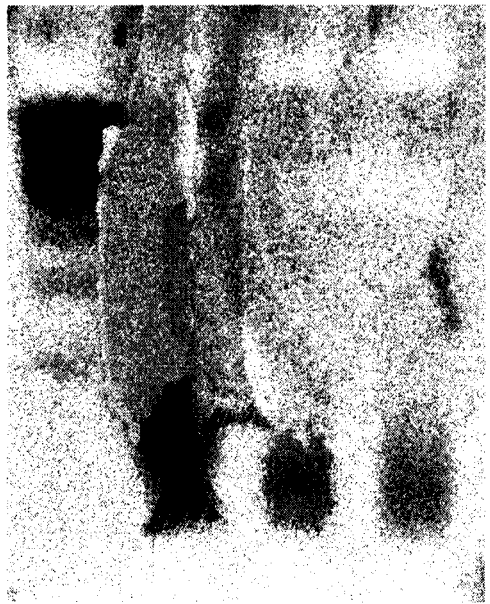
FIG. 2 shows AluI restriction digestion of mimetic target.

SEQ ID NO: 1 and SEQ ID NO: 2 were mixed and allowed to hybridize at room temperature and subsequently subjected to AluI restriction endonuclease (New England Biolabs) digestion in a buffer provided by the enzyme manufacturer at 37° C. A control reaction, not containing AluI enzyme was also produced. As shown in FIG. 2, size fractionation of the digestion products demonstrate that the reaction proceeded to completion and that hybridized duplex Target+Guidance-Primer (lane 2) can be distinguished from digested products (lane 3). Lane 1 of FIG. 2 shows a HindIII digested lambda DNA as a size standard.

Example 4: Rolling Circle Reactions Using Take-Off Probe

Figure 3:
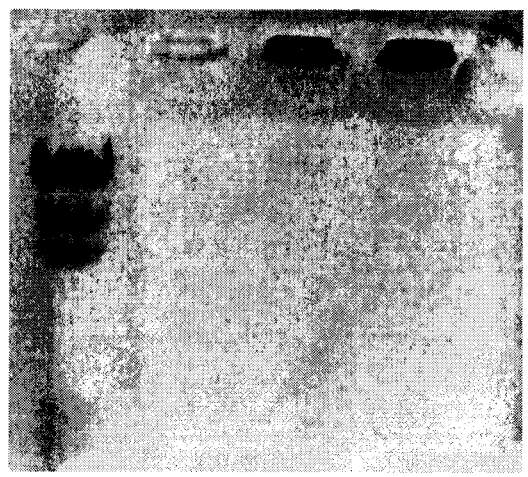
FIG. 3 shows reaction products from Rolling circle reactions using Take-off probe which were fractionated through a 1% agarose gel and visualized by SYBR-Green staining.

A portion of digested template (0, 1, 2 ng) was mixed in a suitable reaction containing 50 nM circular Take-off probe (SEQ ID NO: 3), deoxynucleotide triphosphates and Phi29 DNA polymerase under isothermal conditions maintained at 30° C. for 60 minutes. The reaction products were fractionated through a 1% agarose gel and synthesized products were visualized by SYBR-Green staining. As shown in FIG. 3, no reaction products were visible in lane 2 (which contained 0 ng template), while reaction products were clearly visible in lanes 3 and 4, which contained 1 ng and 2 ng of template respectively.

Example #5: Testing the Requirement for Circularized Take-Off Probe for Isothermal Amplification Take-off probes (SEQ ID NO: 3) which had been circularized or maintained linear were tested for their ability to support isothermal DNA synthesis in the presence of AluI digested target DNA from Example #3. Identical reactions were produced which contained 0, 1, 2 ng/reaction template DNA in the presence of either ligated (wells 2, 3 and 4) or un-ligated Take-off probe (wells 5, 6, 7).

Figure 4:
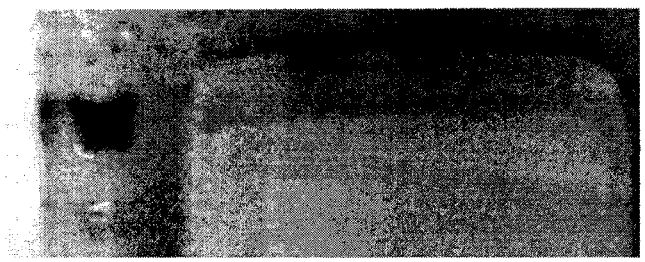
FIG. 4 shows reaction products from testing the requirement for circularized primers to mediate efficient isothermal amplification.

As shown in FIG. 4, synthesized DNA was evident only in lanes containing ligated circularized primer in the presence of template. Following incubation, the reaction products were fractionated through a 1% agarose gel in 1× sodium borate buffer. Synthesized products were visualized by Sybr-Green (Invitrogen) staining as described. Fluorescence was observed under a blue light (470 nm) transilluminator. Lane 1. Contains a HindIII lambda DNA size marker (New England Biolabs). Fluorescence was observed under a blue light (470 nm) transilluminator.

Example #6. Simultaneous Digestion and Rolling Circle Amplification

Figure 5:
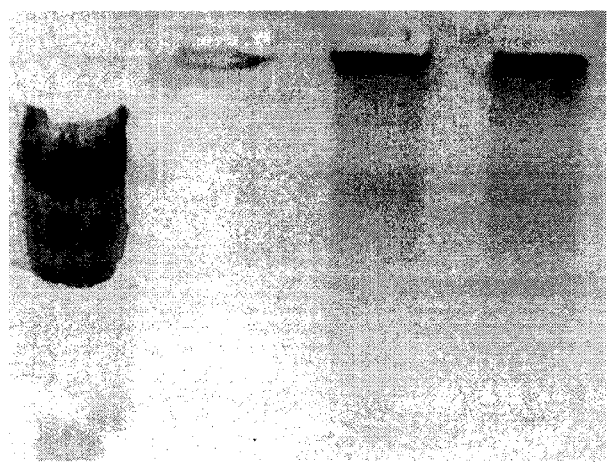
FIG. 5 shows testing results comparing the ability of circularized or linear take-off probes to support isothermal DNA synthesis in the presence of AluI digested target DNA.

The ability of the digestion reaction to proceed in concert with the rolling circle reaction was tested in a buffer which allowed both enzymes to function optimally. DNA synthesis occurring in the presence of 0, 1 or 2 ng template (lanes 2, 3 and 4, respectively) when in the presence of Guidance-primer and take-off probe was evaluated. As shown in FIG. 5, efficient synthesis of DNA by rolling circle amplification under isothermal conditions proceeded effectively when all components were present in one reaction vessel.

Example 7. Using Other DNA Polymerases with the Take-Off Probe

The digested template DNA from Example 3 was tested in a reaction containing Take-off probe (SEQ ID NO: 3) in the presence of Bst DNA polymerase and 0 or 20 ng AluI digested template at 65° C.

Figure 6:
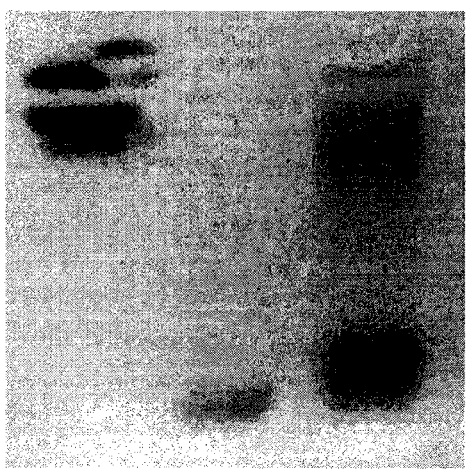
FIG. 6 shows results from assays in which the digestion reaction was allowed to proceed in concert with the rolling circle reaction in a buffer which allowed both enzymes to function optimally.

FIG. 6 shows a rolling circle reaction generated with Bst DNA Polymerase which generates smaller fragments spanning a wider size range as it is not as processive as Phi DNA polymerase.

Alternative enzymes in addition to Phi29 DNA polymerase, such as BST DNA polymerase, therefore appear to efficiently use the Take-off probe in the presence of suitable prepared template to support DNA synthesis by rolling circle isothermal amplification.

The digestions and transcription conditions may be selected based on the preferred temperature ranges of the endonuclease and polymerase. Optionally, the endonuclease and polymerase are selected such as to be active at the same temperature such that the amplification may occur at a single temperature.

For example, with Bst DNA polymerase medicated reactions, the digestion may occur at about 30 degrees Celsius, or about 60 degrees Celsius. If a thermostable endonuclease is used, and the transcription reaction may be mediated at about 60 Celsius.

For reactions using Phi DNA polymerase, the reaction is maintained at about 30 degrees Celsius for about 30-60 minutes.

Example 8. Template Titration and Rolling Circle Amplification

Varying concentrations of template were mixed in a reaction containing Guidance primer, take-off probe and the components necessary for simultaneous digestion and rolling circle amplification. Exemplary reactions contain about 50 nM of circular probe DNA, 100 ng of guidance primer, at least 500 micromolar dNTPs, 2 units of DNA polymerase and 1 unit of restriction endonuclease.

Figure 7:
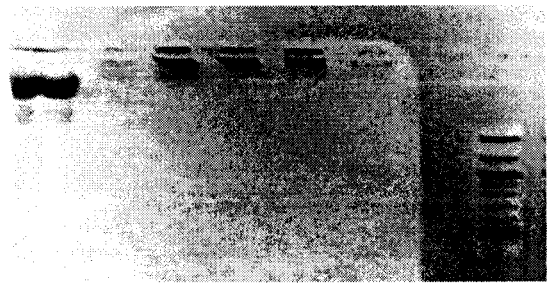
FIG. 7 shows results of an assay in which varying concentrations of template were mixed in a reaction containing Guidance primer, take-off probe and the components necessary for simultaneous digestion and rolling circle amplification.

As shown in FIG. 7, high concentrations of target (100 ng, lane 2) under these conditions are inhibitory, while 10, 1 and 0.1 ng template are clearly detected (lanes 3, 4 and 5 respectively). Lane 6 represents a water blank, while lane 7 represents a negative control which lacks polymerase.

Example 9: Time Course for Rolling Circle Amplification

Time course assays were performed for simultaneous isothermal rolling circle amplification at 30° C. Sufficient master mix was prepared to generate six reactions either lacking (Lanes 1, 3, 5) target or containing (Lanes 2, 4, 6) 10 ng/uL target. The reactions were initiated by adding master mix (containing all the components necessary to initiate a simultaneous digestion and amplification reaction) to their respective tubes and the reactions incubated at 30° C. for 20 minutes, 40 minutes or 60 minutes (Lanes 1 and 2; 3 and 4 and 5 and 6, respectively). The reactions included 10× CutSmart Buffer at 1× final concentration, BSA (10 mg/mL) at 100 ug/mL, variable amounts of Template DNA, 100 ng guidance primer; 500 uM dNTPs; 4 mM mM DTT; 25 nM ligated Circularized DNA; 1 unit/reaction Restriction endonuclease; 1 U Phi29 DNA Polymerase all in a typical reaction volume of 20 microliters brought up to volume with water.

At the requisite time point, a set of tubes was removed and immediately transferred to −20° C. At the completion of the time course, the tubes were thawed, SYBRgreen added and the reaction products fractionated through a 2% agarose/sodium borate buffer gel. Fluorescence was observed under a blue light (470 nm) transilluminator. Lane 8 contains a Lambda HindIII size marker.

TABLE I

Figure 8:
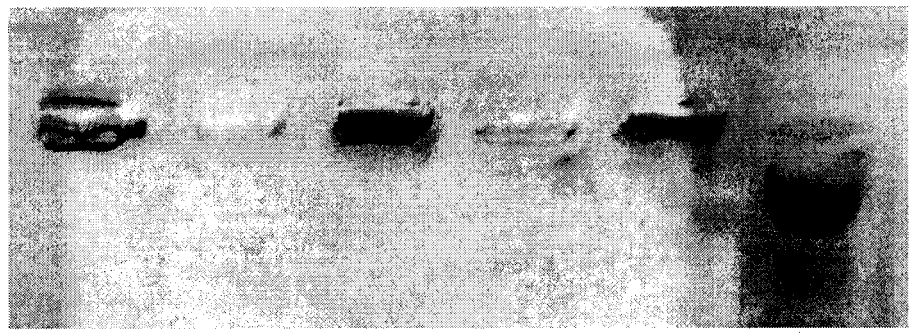
FIG. 8 shows a time course for simultaneous isothermal rolling circle amplification at 30° C.

Lane assignments for shown in FIG. 8.

| Well # | Reaction # | Contents | Incubation time |
|---|---|---|---|
| 1 | 3 | water blank | 20 minutes @ 30° C. |
| 2 | 4 | target | |
| 3 | 5 | water blank | 40 minutes @ 30° C. |
| 4 | 6 | target | |
| 5 | 7 | water blank | 60 minutes @ 30° C. |
| 6 | 8 | target | |
| 7 | lambda DNA marker | / | / |

As shown in FIG. 8, lanes 2, 4 and 6 (10 ng/uL of target) each show the presence of rolling circle amplification products. The amount of amplified product also appears to increase going from the 20 minute incubation (lane 2) to the 40 minute incubation (lane 4).

Example 10: Detection of Genomic Single Stranded Virus

Authentic M13(+) single stranded genomic DNA (~6407 nucleotides) was hybridized to a complementary guidance primer containing an AluI restriction site.

Figure 10A:
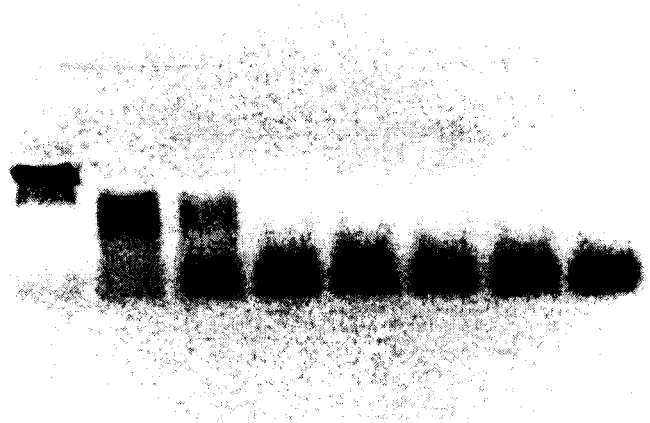
FIGS. 10A and 10B show the amplification of a target sequence using M13(+) genomic DNA.

An AluI restriction endonuclease was then added to the M13(+) and guidance primer mixture and allowed to digest for 30-60 minutes. Following digestion, the DNA was serially diluted. A portion was fractionated through an agarose gel and the digested products visualized by SYBR™ green staining (FIG. 10A).

A circular DNA probe containing a sequence complementary to the upstream portion of an initiation strand generated by AluI digestion was then added to the digests along with a Phi29 DNA polymerase and the reaction was allowed to proceed for 60 minutes.

Figure 10B:
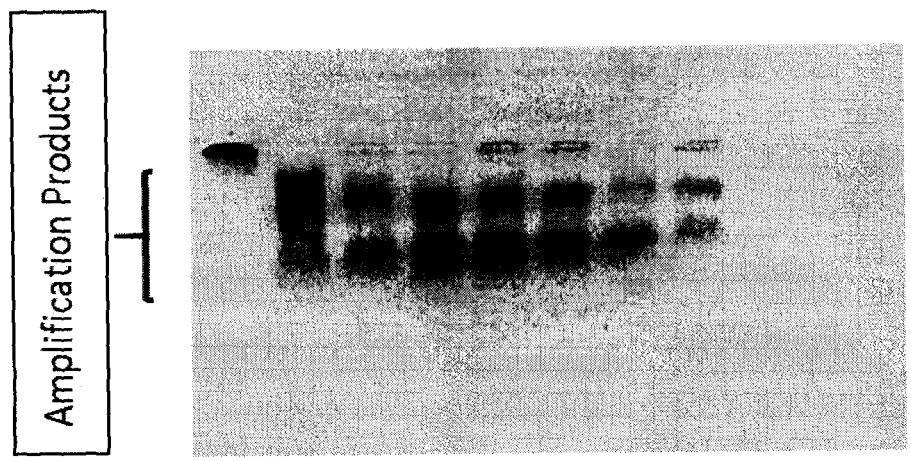

Each serial dilution was then visualized on an agarose gel using SYBR green. As shown in FIG. 10B, amplification products were observed in each fraction that contained M13 genomic DNA that had been contacted with a complementary guidance primer and then digested with AluI before the addition of a master mix (MM) containing a circular DNA probe. No amplification products were observed in the negative control that contained water and MM. The newly observed species in FIG. 10B represent the transcription products resulting from the priming of the circular DNA probe by the guidance primer mediated digestion of the genomic viral DNA.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

The invention claimed is:

1. A method of nucleic acid amplification, comprising:
a) providing a sample comprising a nucleic acid molecule consisting of a single stranded DNA initiation strand, wherein the single stranded DNA initiation strand is a naturally occurring DNA molecule or fragment thereof, or a cDNA produced by reverse transcription of a natural occurring nucleic acid molecule or fragment thereof;
b) generating a double stranded DNA substrate by hybridizing a guidance primer to the initiation strand, wherein the guidance primer is a single stranded DNA molecule comprising a sequence complementary to at least a portion of the initiation strand and wherein the double stranded DNA substrate comprises a recognition site recognized by a site-specific endonuclease;
c) cleaving both strands of the double stranded DNA substrate at the recognition site with the endonuclease wherein the cleaved guidance primer and cleaved initiation strand dissociate to form cleaved single stranded DNA molecules;
d) contacting the cleaved single stranded DNA molecules with a circular DNA probe under conditions that allow for hybridization between complementary sequences of a 3' region of the cleaved guidance primer and the circular DNA probe wherein the 3' region comprises a free 3'-hydroxyl end generated upon cleavage of the substrate by the endonuclease; and
e) generating an amplified nucleic acid product by rolling circle amplification (RCA) wherein steps c), d) and e) occur in a single reaction vessel.

2. The method of claim 1, wherein the guidance primer is a non-naturally occurring synthetic DNA molecule.

3. The method of claim 1, wherein the guidance primer is from 12 to 20 nucleotides in length.

4. The method of claim 1, wherein steps a) to e) occur at the same temperature.

5. The method of claim 4, wherein the temperature is from about 20° C. to about 30° C.

6. The method of claim 1, further comprising the step of detecting the amplified nucleic acid product.

7. The method of claim 6, wherein the amplified nucleic acid product is detected in situ, in gel via electrophoresis, in a lateral flow, in microarray, or on a bead surface.

8. The method of claim 6, wherein the amplified product is detected in situ in real time.

9. A method of detecting the presence of a target nucleic acid sequence in a test sample, wherein the target nucleic acid sequence comprises a recognition site recognized by a site-specific endonuclease, the method comprising:
performing nucleic acid amplification according to the method of claim 6, wherein the sample in step a) is the test sample, and wherein detection of an amplified nucleic acid product indicates the presence of the target nucleic acid sequence in the test sample.

10. The method of claim 9, wherein the test sample is from a subject, the target nucleic acid sequence is associated with a medical condition or pathogenic organism, and the presence of the target nucleic acid sequence in the test sample is indicative of the medical condition or pathogenic organism in the subject or wherein the test sample is an environmental sample, the target nucleic acid is associated with a pathogenic organism, and the presence of the target nucleic acid sequence in the test sample is indicative of the pathogenic organism in the environmental sample.

11. The method of claim 1, wherein the guidance primer is from 8 to 60 nucleotides in length.

12. The method of claim 1, comprising contacting the double stranded DNA substrate in the single reaction vessel with a composition comprising the endonuclease and the circular DNA probe.

13. The method of claim 1, wherein steps b), c), d) and e) occur in the single reaction vessel.

14. The method of claim 13, comprising contacting the single stranded DNA initiation strand in the single reaction vessel with a composition comprising the guidance primer, the site-specific endonuclease and the circular DNA probe.

15. The method of claim 1 wherein the 3' end of the guidance primer is modified to prevent extension of the guidance primer by a polymerase.

16. The method of claim 1, wherein the RCA occurs in the presence of an amplification primer, wherein the amplification primer is a nucleic acid molecule capable of hybridizing to the amplified nucleic acid product and initiating DNA synthesis using the amplified nucleic acid product as template.

17. A method of detecting the presence or absence of a target single stranded DNA initiation strand in a sample, the method comprising:
a) combining in a single reaction vessel the sample and a composition comprising:
i) a guidance primer, wherein the guidance primer is a single stranded DNA molecule between 12 and 60 nucleotides in length and comprises a sequence complementary to at least a portion of the target single stranded DNA initiation strand;
ii) a site specific endonuclease, wherein the site specific endonuclease cleaves a recognition site on a double stranded DNA substrate formed by hybridization of the guidance primer to the target single stranded DNA initiation strand to produce two fragments, wherein the melting temperature of the two fragments is lower than the melting temperature of the double stranded DNA substrate such that the two fragments dissociate to form cleaved single stranded DNA molecules, wherein the cleaved single stranded DNA molecules comprise a cleaved single stranded DNA initiation strand fragment comprising a free 3'-hydroxyl end generated upon cleavage of the substrate by the endonuclease and a cleaved guidance primer fragment comprising a free 3'-hydroxyl end generated upon cleavage of the substrate by the endonuclease;

iii) a circular DNA probe comprising a sequence complementary to a 3' region of the cleaved guidance primer fragment; and iv) a polymerase enzyme, b) wherein the presence of the target single stranded DNA initiation strand in the sample produces the double stranded DNA substrate that is cleaved by the site specific endonuclease to produce the cleaved single stranded DNA molecules, and wherein the cleaved guidance primer fragment hybridizes to the circular DNA probe and primes the rolling circle amplification (RCA) of the circular DNA probe by the polymerase enzyme to produce an amplified nucleic acid product; and b) detecting the presence of the amplified nucleic acid product, wherein the presence of the amplified nucleic acid product is indicative of the target single stranded DNA initiation strand in the sample.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Synthetic

<400> SEQUENCE: 1
cgtttgaagc tcgaatt                                                   17

<210> SEQ ID NO 2
<211> LENGTH: 59
<212> TYPE: DNA
<213> ORGANISM: Artificial Sequence
<220> FEATURE:
<223> OTHER INFORMATION: Synthetic

<400> SEQUENCE: 2
attaagagga agcccgaaag acttcaaata tcgcgtttta attcgagctt caaagcgaa    59
```

```
<210> SEQ ID NO 3
<211> LENGTH: 43
<212> TYPE: DNA
<213> ORGANISM: Artificial Sequence
<220> FEATURE:
<223> OTHER INFORMATION: Synthetic

<400> SEQUENCE: 3
ctcgaattaa aacgcgatat ttgaagtctt tcgggcttcc tct                           43
```